United States Patent
Ullman et al.

(10) Patent No.: US 6,632,606 B1
(45) Date of Patent: Oct. 14, 2003

(54) METHODS FOR SINGLE NUCLEOTIDE POLYMORPHISM DETECTION

(75) Inventors: Edwin F. Ullman, Atherton, CA (US); Sharat Singh, San Jose, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 0 days.

(21) Appl. No.: 09/592,053

(22) Filed: Jun. 12, 2000

(51) Int. Cl.[7] .................... C12Q 1/68; C12P 19/34; C12M 3/00; C07H 21/00
(52) U.S. Cl. .................... 435/6; 435/91.2; 435/288.7; 536/25.32; 536/25.4
(58) Field of Search .................... 435/6, 91.2, 288.7; 536/25.32, 25.4; 422/61

(56) References Cited

U.S. PATENT DOCUMENTS

| | | | |
|---|---|---|---|
| 4,650,750 A | 3/1987 | Giese | 435/7 |
| 4,709,016 A | 11/1987 | Giese | 530/389 |
| 5,360,819 A | 11/1994 | Giese | 514/538 |
| 5,470,705 A | 11/1995 | Grossman | 435/6 |
| 5,514,543 A | 5/1996 | Grossman | 435/6 |
| 5,516,931 A | 5/1996 | Giese | 560/59 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,650,270 A | 7/1997 | Giese | 435/6 |
| 5,703,222 A | 12/1997 | Grossman | 536/24.3 |
| 5,721,099 A * | 2/1998 | Still et al. | 435/6 |
| 5,777,096 A | 7/1998 | Grossman | 536/24.3 |
| 5,807,682 A | 9/1998 | Grossman | 435/6 |
| 5,846,839 A | 12/1998 | Gallop | 436/518 |
| 6,027,890 A | 2/2000 | Ness | 435/6 |
| 6,251,581 B1 | 6/2001 | Ullman | 435/4 |
| 6,312,893 B1 | 11/2001 | Van Ness | 435/6 |
| 6,368,874 B1 | 4/2002 | Gallop | 436/518 |

OTHER PUBLICATIONS

Brookes, "The Essence of SNPs", Gene 234, 1999, 177–186.
Fitch et al., "Improved Methods for Encoding and Decoding Dialkylamine–Encoded Combinatorial Libraries", J. Comb. Chem. 1999, 1, 188–194.
Ni et al., "Versatile Approach to Encoding Eombinatorial Organic Syntheses Using Chemically Robust Secondary Amine Tags", J. Med. Chem. 1996, 39, 1601–1608.
Giese, "Electrophoric Release Tags: Ultrasensitive Molecular Labels Providing Multiplicity", Trends in Analytical Chemistry, vol. 2, No. 7, 1983, 166–168.

* cited by examiner

*Primary Examiner*—Ethan Whisenant
*Assistant Examiner*—Joyce Tung
(74) *Attorney, Agent, or Firm*—Stephen C. Macevicz

(57) ABSTRACT

Methods and compositions are provided for determining large numbers of single nucleotide polymorphisms in target DNA employing particles having (1) primers complementary to sequences in the target DNA where the next succeeding 3'-nucleotide is a potential single nucleotide polymorphism and coding composition members, where the members are unique for each primer, and (2) differentially labeled terminating nucleotides, where the label permits separation of the terminating nucleotides. Desirably the particles are separated into groups having a common prevalent next succeeding nucleotide. The particles and target DNA are combined under nucleotide extending conditions, the particles separated into groups in accordance with the terminating nucleotide and the coding members identified, so that one knows the sequence and the single nucleotide polymorphism. Various protocols are provided for the determination.

8 Claims, No Drawings

METHODS FOR SINGLE NUCLEOTIDE POLYMORPHISM DETECTION

BACKGROUND OF THE INVENTION

1. Field of the Invention

The field of this invention is the detection of the simultaneous detection of large numbers of variations in DNA sequences.

2. Background

Individual susceptibility to disease and environmental toxins, prognosis of existing disease, efficacy of a particular drug, susceptibility to adverse drug reactions, etc., in humans and domestic animals and plants are becoming increasingly predictable by genetic analysis. Many of these characteristics are associated with multiple genes and are not due to a single genetic abnormality. The extensive effort currently devoted to genome sequencing has revealed a strong correlation between sequence polymorphism, particularly base deletions and substitutions and the occurrence of numerous genetic diseases. It has been estimated that single nucleotide polymorphisms occur at about 1 in every 400 nucleotides, a frequency that is continually updated as the human genome is unraveled. Single nucleotide polymorphisms therefore provide a valuable source of genetic markers for determining identity, establishing genetic linkages and predicting/diagnosing disease.

Analysis of single nucleotide polymorphisms (SNP's) is becoming a primary approach for the study of human sequence variation. Routine scoring of SNP's requires the detection of multiple single-nucleotide polymorphisms from one sample, and calls for methods allowing the detection of several single-nucleotide variations in a single analysis.

Polymorphisms in the coding regions of individual genes are often linked to polymorphisms in the neighboring introns. When polymorphisms occur that create or remove restriction sites, the pattern of lengths of DNA that are produced by one or more restriction enzymes is changed giving rise to "restriction fragment length polymorphisms" (RFLP). Thus, changes in the pattern of these fragments, measured by electrophoresis, may reflect familial abnormalities in the adjacent gene. Although RFLP's are very useful for genetic mapping they do not have 100% correlation with coding region polymorphisms and do not readily lend themselves to the evaluation of the large numbers of genes that may affect the particular phenotype. Accordingly, alternative methods that can meet this need are of interest.

One of these methods is screening for large numbers of "single nucleotide polymorphisms" (SNP) either within coding or non-coding regions of the genome. Although the frequency of SNP's in coding regions is lower, their relevance arguably may be greater, at least when they produce a change in the amino acid sequence of the corresponding protein. However methods for finding and screening for SNP's are still relatively primitive.

3. Description of the Related Art

Holland (*Proc. Natl. Acad. Sci. USA* (1991) 88:7276) discloses that the exonuclease activity of the thermostable enzyme *Thermophilus aquaticus* DNA polymerase in PCR amplification to generate specific detectable signal concomitantly with amplification. The TAQMAN assay is discussed by Lee in *Nucleic Acid Research* (1993) 21:16 3761). Marino, *Electrophoresis* (1996) 17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformational polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected.

Pastinen, *Clin. Chem.* (1996) 42:1391 amplifies the target DNA and immobilizes the amplicons. Multiple primers are then allowed to hybridize to sites 3' and contiguous to an SNP site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the SNP. The identity of the base at the SNP site is defined by the triphosphate that is used. A similar approach is taken by Haff, *Nucleic Acids Res.* (1997) 25:3749 except that the sizing is carried out by mass spectroscopy and thus avoids the need for a label. However both methods have the serious limitation that screening for a large number of sites will require large, very pure primers that can have troublesome secondary structures and be very expensive to synthesize.

Hacia, *Nat. Genet.* (1996) 14:441 uses a high density array of oligonucleotides. Labeled DNA samples were allowed to bind to 96,600 20-base oligonucleotides and the binding patterns produced from different individuals were compared. The method is attractive in that SNP's can be directly identified but the cost of the arrays is high. Fan (Oct. 6–8, 1997, IBC, Annapolis Md.) has reported results of a large scale screening of human sequence-tagged sites. The accuracy of single nucleotide polymorphism screening was determined by conventional ABI resequencing. Allele specific oligonucleotide hybridization along with mass spectroscopy has been discussed by Ross in *Anal. Chem.* (1997) 69:4197.

Brenner and Lerner, *PNAS* (1992) 89:5381 suggested that compounds prepared by combinatorial synthesis can each be labeled with a characteristic DNA sequence. If a given compound proves of interest, the corresponding DNA label is amplified by PCR and sequenced, thereby identifying the compound.

W. Clark Still, in U.S. Pat. No. 5,565,324 and in *Accounts of Chem. Res.*, (1996) 29:155, uses a releasable mixture of halocarbons on beads to code for a specific compound on the bead that is produced during synthesis of a combinatorial library. Beads bearing a compound of interest are treated to release the coding molecules and the mixture is analyzed by gas chromatography with flame ionization detection.

SUMMARY OF THE INVENTION

Methods and compositions are provided for substantially concurrently detecting a plurality of single nucleotide polymorphisms (snp's) in DNA, where a plurality of snps is of interest. The method employs as reagents, a mixture of particles, template dependent polynucleotide polymerase, and at least one chain terminating labeled nucleoside triphosphate. The particles are characterized by having a primer nucleic acid sequence, where the particles will have a plurality of primer sequences for different sites associated with snp's and a unique coding composition defining the primer sequence. Depending upon the particular protocol and the number of snps of interest, the coding composition will comprise one or more molecules. In carrying out the method, the reagents and sample are mixed and the primers having snp's corresponding to the chain terminating nucleoside triphosphate extended by one base. Again, depending upon the number of snps of interest and the protocol, the sample may be analyzed in one or more assay mixtures. The particles are identified by means of the label and the primer determined by means of the coding sequence, where with a single coding molecule, the determination can be made using electrokinetic separation. For large numbers of snps, the coding composition may be determined on an individual particle. By having different combinations of coding labels for each of the primers, very large numbers of snps may be determined in a single operation. Kits can be provided of the reagents for convenience to the user.

DESCRIPTION OF THE SPECIFIC EMBODIMENTS

In accordance with the subject invention, a rapid and accurate method is provided for detecting a plurality of single nucleotide polymorphisms in a nucleic acid sample. The method employs as reagents, a mixture of particles, template dependent polynucleotide polymerase, and at least one chain terminating labeled nucleoside triphosphate. The particles have a primer which hybridizes to a target sequence which has a snp at the 5' end of the target sequence (the primer is 3' of the snp in relation to the sequence to which it hybridizes and the snp is 3' of the primer sequence) and a coding composition, which coding composition has one or more entities which can be determined free of the particle. Each coding composition in the mixture of particles is unique for the primer bound to the same particle to which the coding composition is bound.

The protocols which are employed will depend on the number of snps to be determined from a single sample. There will usually be at least 10 snps of interest, more usually at least 50, frequently at least 100 or more. Up to about $10^4$–$10^5$ snps, one may use a single molecule for the coding composition. With a single molecule, one may select to determine all of the members of the coding composition for the different primers in a single determination. Above that amount, one may use a combination of molecules in the coding composition. In this situation, one will usually do a determination with a single particle.

The particles which are employed may be of any convenient material, depending on the protocol, may be magnetic or magnetizable, e.g., superparamagnetic, or non-magnetic, may be organic or inorganic, such as organic polymers, e.g., latex, inorganic compositions, e.g., silica, silicon, Bioglas, charcoal, gold, etc., so long as they are functionalizable to allow for the binding of the various components to the particles and their properties are compatible with the protocols of this invention. The particles will generally be of a size having a diameter in the range of about 50 nm to 500µ more usually in the range of about 100 nm to 100 µp.

The particle may have any density, but preferably of a density approximating water, generally from about 0.7 to about 1.5 g/ml. The particles may or may not have a charge. The particles may be magnetic, non-magnetic or paramagnetic. The particles may be solid (e.g., comprised of organic and inorganic polymers or latex), oil droplets (e.g., hydrocarbon, fluorocarbon, silicon fluid), or vesicles (e.g., synthetic such as phospholipid or natural, such as cells and cell ghosts).

The solid particles are conveniently organic polymers, either addition or condensation polymers, which are readily dispersible in a reaction medium. The solid particles will also be adsorptive or have reactive sites for chemical reaction, so as to bind or attach at their surface, either directly or indirectly, the primer and the coding composition members. Entities which may be bound include members of a specific binding pair complex, linkers which permit release of one of these entities, and the like. By specific binding pair is intended a pair of molecules that have an affinity for each other of at least $10^6$, more usually at least $10^7$, or greater. These include receptors and ligands, polysaccharides and lectins, antibodies and ligands, hybridizable nucleic acid strands, enzymes and substrates or inhibitors, etc. The solid particles can be comprised of polystyrene, polyacrylamide, homopolymers and copolymers of derivatives of acrylate and methacrylate, particularly esters and amides, silicones and the like.

Since the individual stages of the protocols employed this invention have in substantial part found previous use, a number of known different particles may be employed. Bonded to each particle is a primer of known sequence, where it is known that 3' of the sequence in the strand to which the primer binds, there is an snp. Generally, the number of primers per particle will be at least one and up to about $10^7$, more usually up to about $10^5$, frequently not more than about $10^4$. The primers will have at least 12 nucleotides in the hybridizing sequence, more usually at least about 15, preferably in the range of about 18 to 50, more preferably in the range of about 18 to 36. The primers may all be of about the same size, usually not differing by more than a factor of 10, more usually not more than a factor of 5, from the average size of the primers. Conveniently, the largest primer would not be more than about 8 times the smallest primer, frequently not more than 5 times the smallest primer, frequently not more than 3 times the smallest primer.

Since the natural nucleotides are readily available, normally the primers will be made of the natural nucleotides, although synthetic nucleotides, which, provide the desired affinity may find use in appropriate situations. For the most part, there will be no advantage in substituting unnatural bases or nucleotides for the natural bases or nucleotides.

The primers will conveniently be joined to the particles by a flexible chain, so that they are readily available for binding to the DNA in the sample. Various linking groups have found use, a number of them associated with the synthesis of DNA sequences. As appropriate, the primers may be synthesized on the particle or bonded to the particle using appropriate chemistries. See, for example, U.S. Pat. No. 5,565,324. Linkers will generally be of at least about 6 carbon atoms and not more than about 60 carbon atoms and have a variety of heteroatoms and heterofunctionalities, such as oxy, oxo, non-oxo-carbonyl, acyl, both organic and inorganic, e.g carboxy, phosphoryl, sulfonyl, etc., and ester and amide derivatives thereof, amino, cyano, thio, etc. The groups may be aliphatic, alicyclic, aromatic, heterocyclic and combinations thereof.

In addition to the primers, a coding composition will be employed which will be unique for each primer composition. The coding composition will have at least one member and not more than about four members, usually not more than about three members. The choice of the coding composition, the nature of the entities comprising the coding composition, and the number of entities in the coding composition will be governed, in part, by the number of different primers present on the particles.

For a smaller number of different primers, that is fewer than about $10^4$–$10^5$, usually a single unique member will be present on the particles to define the primer. While various compositions may be employed for the primers, desirably the members of the coding composition will be distinguishable by their electrokinetic properties. Thus, the members may differ as to charge, molecular weight or other characteristic which allows for their separation and detection by electrokinetic separation. The coding composition entities may be further distinguishable by varying the conditions of the electrokinetic separation, such as pH, ionic strength, redox potential, etc. Also, they may bind differently to various entities, as specific binding pairs, to change their migratory rate. In addition, to their differences in their migratory aptitude in electrokinetic separation, they may also be distinguished by a detectable label or a functionality, which allows for separate reactions for the different members of the coding composition. Thus, one may have two members of coding compositions, which would not otherwise be distinguishable, except that they are labeled differently, e.g. radioisotopes, fluorophores, chemiluminescers, etc. or have two different functionalities which allow for differential substitution, such as different fluorophores or fluorophore combinations. Thus, one could have functionalities, protected or unprotected, such as hydroxy, carboxy, amino, thiol, etc., where different functionalities may be individually reacted with different detectable labels, providing for a different detectable signal, e.g., different wavelengths.

The coding composition members may be sequencable, e.g. oligonucleotides, polyamides, etc., or non-sequencable, substituted aliphatic groups, where the substituent may be any substituent which provides for electrokinetic discrimination, e.g. halo, such as fluoro, chloro, bromo and iodo, cyano, nitro, hydroxy, substituted hydroxy, such as ethers and esters, amino, substituted amino, such as alkyl, amides, and imines, etc. Desirably, the coding composition members should be readily available or easily synthesized, stable under the conditions of the protocol, and can be readily attached to and released from the particles.

Conveniently oligos and modified oligos may be prepared, since they provide for the opportunity to have a graduated mass and differences in the number and/or type of charges. The differences between the oligos should allow for ease of detection and should be capable of differentiation by electrokinesis. Since the capabilities of electrokinetic separation and detection are continually improving, there is no minimum level of differentiation, generally spacing of 0.05 mm or less should suffice.

Polynucleotides up to about 1500 nucleotides can be separated today by electrokinesis and improvements should allow for even larger polynucleotides to be independently distinguished in a single electropherogram. Other compounds which may find use include dendrimers, oligosaccharides, polycyclics, polyketides, etc.

Generally, the coding composition entities will be of at least 100 Dal and less than about 50 kDal, usually less than about 30 kDal, and preferably less than about 20 kDal, where sequencable entities will be into the higher molecular weights. Generally, the individual members will differ in molecular weight by about 10 Dal, usually by about 15 Dal and more frequently by about 20 Dal. The differentiation will be affected by their mass, charges present in the member, folding which may affect the migratory aptitude, and the nature of the detectable label, the sequencable entities usually differing by the molecular weight of a monomeric unit, e.g. about 70 to about 500 Dal.

The use of oligonucleotides has a special capability, in that each oligonucleotide may be amplified. The probe may be a single strand, which is releasable from the particle, or may be hybridized with a complementary oligonucleotide after hybridizing with the target DNA, where the coding composition member strand remains bound to the particle and the other strand may be released by denaturation. This allows for very small amounts of the coding members to be present, since the coding members may be amplified, either on the particle, or preferably released from the particle. By having the primer bound by a linker, which allows for release under conditions other than release of the coding members, the two different groups of molecules can be separately isolated and analyzed. In addition, during the amplification, detectable labels may be introduced into the coding members, by using labeled primers, labeled nucleotide triphosphates, or providing for a functionality which can be reacted with a detectable label.

The number of molecules of the coding composition may be greatly amplified by linking the particles to hydrophilic polymers, such as polysaccharides, polyvinyl alcohols, etc., generally under about $10^7$ molecular weight, where the hydrophilic polymer may be highly functionalized, having a coding composition molecule in the range of from about 1:5–20 per monomeric unit. Thus., for each binding event, there would be a large number of coding composition molecules for detection.

Where a single coding composition entity is used, the nature of the entities may be varied widely. Thus, one may use at the same time on different particles, oligonucleotides, oligopeptides, small organic molecules, where the molecules may be charged or uncharged, so as to allow for differentiation under eletrophoretic and electroosmotic conditions, and the like. In addition, one could have the same entity linked by a different releasable linkage to the particle, where the different releasable linkage permits differential reaction with different labels. For example, if the functionalities were amino and thiol, one could react the amino group with a carboxy of one fluorophore and the thiol with a maleimido of a different fluorophore. With polynucleotides, one can distinguish single base differences up to about 1500 nucleotides, so that with four different fluorophores, one could distinguish 6000 different primers. By using an additional number of distinguishable fluorophores, the number of primers, which could be determined, would be further increased. By having polypeptides, one could add additional coding composition entities and by having a separation step, separating the polypeptides from the polynucleotides, any interference between the two types of compounds in an electrokinetic separation could be obviated. Separation would be readily achievable using ion exchange columns, random oligonucleotides bound to a support, chelating agents, etc.

Where one uses a plurality of coding composition entities for each primer, the number of primers for which coding entities may be employed, may be greatly expanded above $10^5$, being as large as $10^6$ or greater. The number of different primers and particles becomes an issue of the number of snps of interest and handling of the particles. When using a plurality of coding composition entities per primer, and having overlap as to one of the entities in different coding compositions, the coding composition of each of the individual particles will have to be determined. In this situation the protocol for the determination will be modified.

A different approach is to use lathanide dyes as dopants for the particles. Thus one can use the fluorescent lanthanide metal chelates of terbium, europium, dysprosium, and samarium, where the chelating compounds may be exemplified by bipyridyl and salicylic acid, and acceptor compounds by squarate with europium, and rubrene with terbium to modify the emission wavelength. The emission wavelengths for the lanthanides are: Dy, 576 nm, Tb, 547 nm, Eu, 613 nm and Sm, 646 nm. By employing combinations of two or more of the different fluorescent lanthanide chelates, where the emission band is different for each of the chelates, one can provide a unique profile for each particle. The ratio of the height or area under the peaks at the different wavelengths will be distinctive for each particle. By isolating individual particles and determining their fluorescent pattern, the primer sequence can be identified.

Releasable functionality

The nature of the releasable link may be varied widely. Numerous linkages are available, which are thermally, photolytically or chemically labile. See, for example, U.S. Pat. No. 5,721,099. Where detachment of the product is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an α-chloroether is formed. This may then be coupled with an hydroxy functionality on the bead to form the acetal. Various photolabile linkages may be employed, such as o-nitrobenzyl, 7-nitroindanyl, 2-nitrobenzhydryl ethers or esters, etc.

Esters and amides may serve as linkers, where half-acid esters or amides are formed, particularly with cyclic anhydrides, followed by reaction with hydroxyl or amino functionalities on the bead, using a coupling agent such as a carbodiimide. Peptides may be used as linkers, where the sequence is subject to enzymatic hydrolysis, particularly where the enzyme recognizes a specific sequence. Carbonates and carbamates may be prepared using carbonic acid derivatives, e.g. phosgene, carbonyl diimidazole, etc. and a mild base. The link may be cleaved using acid, base or a strong reductant, e.g., $LiAlH_4$, particularly for the carbonate esters. For a list of cleavable linkages, see, for example, Greene and Wuts, Protective Groups in Organic Synthesis, $2^{nd}$ ed. Wiley, 1991. The versatility of the various systems that have been developed allows for broad variation in the conditions for attachment of coding composition entities and differential detachment of the coding composition entities.

Various functionalities for cleavage are illustrated by: silyl groups being cleaved with fluoride oxidation, acid, bromine or chlorine; o-nitrobenzyl with light; catechols with cerium salts; olefins with ozone, permanganate or osmium tetroxide; furans with oxygen or bromine in methanol; tertiary alcohols with acid; ketals and acetals with acid; α- and β-substituted ethers and esters with base, where the substituent is an electron withdrawing group, e.g., sulfone, sulfoxide, ketone, etc., and the like Linker The choice of linker for the coding composition member will be part of the coding strategy, since the linking group can result in a residual functionality on the product. It may be feasible to further modify the coding member after detachment from the particle, for example by adding a molecule, which is detectable to the available functionality. In designing the synthetic strategy, one can use a functionality to be retained in the member as the point of attachment for the linking group. Alternatively, when permitted by the nature of the member, one could use a cleavage or detachment method, which removes the linking functionality, e.g., an arylthioether or silyl with a metal hydride or acid.

For linking of the coding composition members to the particle, one may employ functionalities, which are present on the particle to form covalent bonds or use functionalities, which randomly bond to the particle. The particle may have a plurality of hydroxyl, thiol, carboxy or amino groups, which may serve as sites for bonding the coding composition members, as well as the primer. Thus, one may form esters, amides, ethers, thioethers, disulfides, etc., where one may use active halogen or pseudohalogen, e.g., benzyl halides, ∀-haloketones, thiol, to react with the functionality on the particle for covalent bonding.

Alternatively, binding of the coding composition members to the particle may involve carbenes and nitrenes, which can insert between a carbon and hydrogen atom to form a covalent bond, or into an olefinic bond to form a cyclopropane (in the case of carbene) or an aziridine (in the case of nitrene). With carbene or nitrene linking groups various substituted benzenes may be used, where the benzene is substituted with a group capable of providing a carbene: $CHN_2$, $COCHN_2$, $SO_2$ $CHN_2$; or nitrene: $N_3$, $NO_2NO$, $SO_2N_3$. The carbenes may be generated from diazo alkane derivatives by photolysis, thermolysis, or by treatment with low valent transition metal species, e.g., $Rh(OAc)_2$. The nitrene may be generated by photolysis or thermolysis from azides; and from nitro, nitroso and azides by using tervalent phosphorus compounds or low valent transition metals. A group of linker moieties of interest for random insertion include 2-nitro-4-carboxybenzyloxy, 2-nitro-4-diazoacetylbenzyloxy, 4- or 5-azidomethylcarbonyl-2-methoxyphenoxy, and 2-methoxy-4, or 5-carboxyphenoxy moieties.

Illustrative compounds where T represents the coding composition member, Z represents a carbene or nitrene precursor or a carboxy group, and R is H or lower alkyl are as follows. For photochemical tag detachment (e.g., with ultraviolet light at about 350 nm): T 3-Z-2-nitrobenzyl ether, T 4-Z-2-nitrobenzyl ether, T 5-Z-2-nitrobenzyl ether, T 6-Z-2-nitrobenzyl ether, T 2-Z-4-nitrobenzyl ether, T 3-Z-4-nitrobenzyl ether, T 3-Z-2-nitrobenzyl carbonate, T 4-Z-2-nitrobenzyl carbonate, T 5-Z-Z-nitrobenzyl carbonate, T 6-Z-Z-nitrobenzyl carbonate, T 2-Z-4-nitrobenzyl carbonate, and T 3-Z-4-nitrobenzyl carbonate. For oxidative detachment (e.g., using ceric ammonium nitrate): 1-OT-2-OR-3-Z-benzene, 1-OT-2-OR-4-Z-benzene, 1-OT-2-OR-5-Z-benzene, 1-OT-2-OR-6-Z-benzene, 1-OT-4-OR-2-Z-benzene, and 1-OT-4-OR-3-Z-benzene. For reductive or alkylative detachment (e.g. with lithium/ammonia or methyl iodide): T (2-Z-phenyl)thioether, T (3-Z-phenyl)thioether, and T (4-Z-phenyl)thioether. For desilylative detachment (e.g., using tetrabutyl ammonium fluoride or acid): T dialkyl-(2-Z-phenyl)silyl ether, T dialkyl-(3-Z-phenyl)silyl ether, T dialkyl-(4-Z-phenyl)silyl ether, T dialkyl-(2-Z-phenyl)silane, T-dialkyl-(3-Z-phenyl)silane, and T-dialkyl-(4-Z-phenyl)silane. Various synthetic techniques may be employed for attaching the coding composition member to the linking member.

Terminating nucleotide

The terminating nucleotide may be any nucleotide, which inhibits further extension of the primer. Commonly, dideoxynucleotides are used, but any nucleotide, where the 3' hydroxy of the deoxyribosyl is unavailable, e.g., ether, or a different sugar is employed, e.g. arabinose, or a group is employed to connect the sugar and base which is not recognized by the polymerase. However, since the dideoxynucleotides are commercially available, even as labeled dideoxynucleotides, and work efficiently in the subject system, the discussion will be directed primarily to these terminating entities. Any terminating group may be used which specifically hybridizes to the complementary base in the template strand and can be labeled to be detectable.

Labels

In the subject invention, there will be segregation of primers by the particular terminating nucleotide. In the protocol using a plurality of coding composition members, the terminating nucleotide will be labeled, with a label, which allows for separation. For the protocol using a single member of the coding composition, one may or may not provide a label for separation. Usually, the label will be a small molecule in the range of about 100 to 500 Dal, which is a ligand member of a specific binding pair. The label will allow for separation of the primers, which have been extended and by using different labels for the different nucleotides, one may separate the particles in accordance with the nature of the snp.

For detecting the coding composition members, the label, is a functionality, which is a detectable moiety, can bind to a compound for separation; as described above, or to a compound, which is detectable. The label should be less than about 2 kDal, preferably less than about 1 kDal, although where combinations of detectable labels, such as fluorophores used for energy transfer are involved, the two fluorophores and the linking group may exceed 2 kDal, usually not exceeding 5 kDal. The label may be a radioisotope, fluorophore, chemiluminescer, or other detectable small molecule. Combinations of energy transfer fluorophores may be used, so as to allow for a single or dual excitation light source. A wide variety of fluorophores have found use, based on fluorescein, rhodamine, Texas red, TOTO, YOYO, etc. These compounds are available with functional groups, which can react with functionalities on the terminating base to provide for a labeled terminating base, either before or after the terminating base is bound to the primer. However, where the coding composition members are determined from an individual particle, the coding composition members may be detected by any means, which may or may not require the presence of a particular detectable label.

Protocols

For carrying out the process, the particles are preprepared. Thus, the particles will have the specific primer and the coding composition members bound to each particle, ready for use for detecting any snps in the nucleic acid sample. The analysis mixture will have conditions appropriate for hyrbridizing the nucleic acid moieties present in the sample to the primers present on the particles. The nucleic acid fragments will usually be at least about 20 nt, more usually at least about 40 nt and not more than about 10knt, usually not more than about 5 knt. The particular size is primarily one of convenience and handling, where the fragment may have only one snp or a plurality of snps. The fragments may be prepared by mechanical disruption, enzyme digestion, chemical fragmentation, or the like. Conveniently, restriction enzymes may be used, particularly ones that cut frequently, such as restriction enzymes that have four nucleotide recognition sites, although restriction enzymes having six nucleotide recognition sites or more may also find use.

The nucleic acid mixture may be derived from an entire nucleus, individual chromosomes, amplified fragments, libraries, etc. The nucleic acid, if present in double stranded form, is denatured to provide single strands. While there are many ways to denature double stranded DNA, heat at about 75 to 90° C. for sufficient time for the strands to separate is preferred. The solution may then be cooled. Depending on the nature of the sample, it may be desirable to amplify the DNA sample, using primers, which will increase the amount of target DNA in the sample. Methods for amplification include PCR, single primer amplification, LCR, NASBA, 3SR and so forth. The primers, which are used for expanding the DNA may also be the same as the primers which are used to identify the snps or the primers may be 5' of the snp site. Where a number of snps are present in a polynuclotide, a single primer may be used to amplify the region having the multiple snps.

To the single stranded nucleic acid target sample, the following are provided in combination in an amplification medium: (i) reagents for amplifying each of the polynucleotides and (ii) an oligonucleotide probe for each of the polynucleotides, wherein each of the oligonucleotide probes has a complementary sequence which hybridizes to a region in the target DNA and may have a label for isolating the DNA, which is target DNA, from the other DNA in the sample, and (iii) each of the nucleotide triphosphates. In many instances, neither the amplification, nor the isolation will be required to obtain the sensitivity desired for the subject identification of snps. However, there may be situations where the sample DNA is sufficiently small, that using present technology, one might not accurately detect the snp.

For assaying for snps, one would add the particles to the target DNA, which target DNA may have been previously amplified. Where amplification has been employed, the target DNA should be separated from the nucleoside triphosphates. Depending on the protocol, different reaction mixtures would be used.

The protocols involve separations or segregations, before or after extension. In performing the determination, one can separate the particles by the particular niucleotide which will be extended for the prevalent sequence and/or the particular terminating nucleotide. One combines: (1) an appropriate nucleotide adding enzyme, e.g., a polymerase or ligase, for adding the complementary terminating nucleotide, e.g., dideoxyriucleotide; (2) one or more of the terminating nucleotides depending on whether one has assay mixtures with multiple terminating nucleotides or individual assay mixtures for each of the four individual terminating nucleotides; and (3) particles, which may have been separated by the nature of the prevalent succeeding nucleotide of the primers. One may have four different reaction mixtures, where the particles are segregated by the primers having a common prevalent nucleotide, and add only the terminating nucleotides which would bind to snps or a single terminating nucleotide which would bind to snps. Where the three terminating nucleotides are added, each of the terminating nucleotides would have a different label allowing for the segregation of the particles by the particular terminating nucleotide.

Alternatively, one could have four reaction mixtures, where one added a different terminating nucleotide in each of the reaction mixtures, without having segregated the particles. In this situation, one avoids the additional separation step, but will include the prevalent nucleotide being extended as well as the snps for the different primers. All primers where the next nucleotide is the same would be extended, whether the prevalent nucleotide or a snp.

If one wished, one could have 12 reaction mixtures, where one would segregate each of the particles by the nature of the prevalent succeeding nucleotide and add a single terminating nucleotide. In this way, subsequent separations are obviated, by performing the separations prior to carrying out the extension.

Of course, where there may be two or more nucleotides at a particular position as a snp, or where there are two prevalent nucleotides, in each case, each of the possibilities will be treated as if they were a single possibility. In the these situations, there will be some redundancy, in that the same primer will be in two different mixtures and there will be a primer associated with a co-prevalent sequence extended by a terminal nucleotide.

The choice of the protocol will depend upon the number of snps one wishes to determine, the degree to which the presence of the coding members of the primers for the prevalent target DNA interferes with the determination of the coding members of the primers for the snps, the number of coding members in the coding composition, and the manner of determination of the coding members.

Identification of the terminating nucleotide is provided by carrying out separate assay mixtures for each of the terminating nucleotides, providing separate labels bonded to each of the terminating nucleotides for separating the particles in accordance with the nature of the terminating nucleotide or performing each of the assay mixtures where only one terminating nucleotide is added for the snps which are present in the mixture. Various specific binding members can be employed, which allow for separation, such as biotin-strepavidin, digoxin-antidigoxin, fluorescein-antifluorescein, 2,4-dinitrobenzene-anti-(2,4-dinitrobenzene),etc. Alternatively, one may use physical separations by employing different fluorescers having different wavelength emission ranges and separating with a fluorescence activated cell sorter or other means. Therefore, there will be four different mixtures of particles, where the particles will have primers extended by the same terminating nucleotide. In addition, in carrying out the protocol, it may be desirable to release the extended-primer particles, in order to separate them away from particles which are contaminating the mixture. One may then use an alternative ligand, which is competitive with the ligand bound to the ddNTP. Desirably, one would use a ligand bound to the ddNTP, which has a lower binding affinity than the ligand used to displace the extended-primer particle. For example, one could use dethiobiotin instead of biotin as the ligand, ouabain or digoxigenin instead of digoxin as the ligand, a modified fluorescein instead of fluorescein and a modified 2,4-dinitrobenzene, e.g. 6-fluoro-2,4-dinitrobenzene instead of 2,4-dinitrobenzene. By employing monoclonal antibodies, one may select for those monoclonal antibodies which have the desired cross-reactivity, where the affinities differ by at least one order of magnitude, differing generally in the range of about $10^{1-4}$, more usually in the range of about $5 \times 10^{1-3}$.

In carrying out the single nucleotide extension, generally, an aqueous medium is employed. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent. The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention, but in individual methods one buffer may be preferred over another.

The reaction is conducted for a time sufficient to extend substantially all of the primers present in the mixture. Generally, the time period for conducting the entire method will be from about 10 to 200 minutes, where, desirably the minimum time necessary will be employed.

The concentration of the nucleotide polymerase may be determined empirically, generally being in the range of about 1 to 20 U/$\mu$l. See, for example, Mullis, et al., Methods in Enzymology (1987) 155, 335. The amount of the target DNA will be varied widely, generally ranging from about 1 to $10^5$, more usually 10 to $10^4$ moles per mole of primer. The amount of primer will be at least about 10pmoles, usually at least about 0.1 $\mu$mole, preferably at least about 1 $\mu$mole and usually not more than about 10mmoles, but any upper limit may be used depending on the number of primers present on a particle and the handling associated with the particles in a liquid medium. The terminating nucleotides will be at least equal to and usually in substantial excess of the total number of primers present in the medium, generally being in at least about 2-fold excess, more usually in at least about 5-fold excess. The concentration of each of the terminating nucleotides will generally in the range of about 0.1 to 10 $\mu$M.

The order of combining of the various reagents to form the combination may vary usually, the sample containing the single stranded polynucleotides is combined with a pre-prepared combination of nucleoside triphosphates and nucleotide polymerase in the presence of the primers. The particles comprising the primers is usually combined with the sample prior to the addition of the other reagents. However, simultaneous addition of all of the above, as well as other step-wise or sequential orders of addition, may be employed. Preferably, the primers are allowed to hybridize to the target DNA prior to the addition of the other reagents. Hybridizing primers are extended by a single nucleotide, where, if required, each terminating nucleotide may allow for separation of the particles into four different mixtures, based on the particular nucleotide. The hybridization and extension is generally performed at a temperature in the range of about 50° C. to about 80° C., preferably, about 50° C. to about 60° C.

At the completion of the extension, the particles are segregated by the particular terminal nucleotide. No separation will be required where one has divided the particles into twelve assay mixtures, segregating the particles by the common prevalent nucleotide and the terminating nucleotide. One may separate the target DNA from the particles, before or after the segregation of the particles in accordance with the terminating nucleotide. The presence of the target DNA will usually be undesirable, but the target DNA may be retained. Separation from the target DNA can be readily achieved by denaturation with heat, ionic strength, solvents, etc., followed by cooling and isolation of the particles free of the target DNA.

As indicated, one could at this stage introduce a purification step. The segregation could involve binding to a solid surface, which could be the wall of a container, particles, e.g. magnetic particles or other particles which allow for segregation, e.g. ligand bound particles to allow for capture by surface bound antiligand, etc. Once the extended-primer particles have been segregated and bound to a surface, they may be released, as described above, but using a displacing ligand, so that only extended-primer particles will be released. These particles may be harvested as an enriched fraction.

In addition, one may use magnetic particles, which have oligonucleotides which are complementary to the extended primer. One may provide for a few extra nucleotides associated with the primer to which the complementary oligonucleotides also bind to enhance the affinity for displacement of the target nucleic acid from the extended primer. One would combine the two particle compositions, the extended-primer particles and the capturing particles, under denaturing and then hybridizing conditions, whereby, the target DNA would be displaced and the extended primer hybridized to the capturing oligonucleotide. These particles would have a low mole ratio to the number of extended-primer particles to minimize formation of large aggregates of particles through the cross-linking that would be available based on the copies of the extended primer and the copies of complementary oligonucleotides on their respective particles. While the optimum number would be determined empirically, the ratio should not be greater than about 20, preferably not greater than about 10, and more preferably not more than about 5. The magnetic particles would be of about the same size as the primer comprising particles and the two groups of particles could be combined with agitation and allowed to incubate for a sufficient time to hybridize, generally less than about 24 h. more usually less than about 12 h.

The capturing particles would be prepared in substantially the same way as the primer comprising particles, In fact, one could have the capturing particles carrying the coding composition, rather than the primer comprising particles, since the two particles are related, in that one oligonucleotide is the complement of the other and the snp is defined, it is only a matter of defining the primer. Alternatively, one could have the coding composition only on the primer comprising particles or on both types of particles. By using magnetic particles, one can provide for enhancement of the extended-primer particles separated particles which have not had the primer extended, but have remained as contaminants of the extended-primer particles. By having magnetic capturing particles, the magnetic particles may be isolated and washed to ensure the substantially complete absence of primer comprising particles which have unextended primers. In this manner the potential for false positives in detecting coding compositions of particles with primers which have not undergone extension is further diminished.

The protocols now diverge, depending on whether the method involves assaying for a mixture of coding members, each one being unique and defining the primers which were extended by the particular terminal nucleotide or assaying as to each particle, where the particles are individually segregated.

Where a mixture of coding members is to be determined, the coding members are released in accordance with the nature of the releasable or labile linkage. As indicated previously, one may use light, heat, enzymes or chemical reagents to provide for the release. Also, as previously indicated, where the coding members do not have a detectable label, a label will be bonded to the coding members to permit their detection.

The single unique members associated with each primer allow for electrokinetic separation. One releases the coding members from the particles as a mixture of coding members. After release, one has a solution of a mixture of coding members, where a single coding member is associated with a specific primer. The mixture is then subjected to analysis.

For the most part, the analytical method will be capillary electrophoresis, where each of the coding members will be separated by electrokinesis into specific bands and may be read. Since each coding member is unique, one will obtain an electropherogram of all of the coding members associated with primers, which were extended, so that the presence of any snps can be readily determined. Since one knows the prevalent base for a particular primer, the presence of coding members for the particular primer associated with a different base indicates the presence of the snp. Where there may be ambiguity as to a particular snp, in that one or more nucleotides may be substituted for the prevalent nucleotide, and the difference is of importance, one would provide a protocol which separates the particles by the added nucleotide, by having different labels on the terminating nucleotide, and then release the coding composition members.

The conditions of the capillary electrophoresis separation are conventional and can be substantially the same as use for DNA sequencing. Generally, the voltage will be in the range of about 400 to 4000 volts across the capillary. Various buffers may be used for the separation, such as HEPES, MES, TRIS, acetate, borate, etc., generally at a concentration of about 0.5 to 25 mM. Depending on the nature of the microfluidic device, various polymeric materials may be included in the capillary channel, e.g. polyacrylamide gel, agarose, hydroxyalkylcellulose, etc., for size and charge separation. Capillary devices are known, see, for example, Analytical Chemistry (1996) 68:4081–4086.

Where the number of snps is large and one has used multiple members as the coding composition for a single primer, then the protocol will involve separation of the particles as single particles. In this protocol, one would have the terminating nucleotides labeled with a specific binding member, usually a small molecule. After preparing the assay mixtures, where the particles are separated by the primers having a common prevalent succeeding nucleotide, and potentially separating as well by a common terminating nucleotide for a snp, the protocol proceeds in the former case by adding the three terminating nucleotides other than the prevalent nucleotide. The protocol then proceeds substantially as described above.

However, after the extension, particles, particularly magnetic particles for convenience, having the complementary member of the specific binding member label, are added. Each of the terminating nucleotides would have different labels, so that by successively adding particles having the complementary members for the different labels, after separation, there would result four different mixtures, each one having common snps. The magnetic particles may now be separated from particles which do not have the magnetic particles attached. Each of the particles may be separated individually and the coding members read. Since one knows the terminating nucleotide and the coding members will inform as to the primer, the different snps are determined. By having combinations of coding members, very large numbers of snps may be determined from a single sample. Where the amount of sample is small, the method allows for a single use of the sample with only a four fold division. The coding members may be readily determined by the nature of their label by any convenient means, such as mass spectrometry, gas chromatography, HPLC, capillary electrophoresis, etc. Where the coding molecule is an oligonucleotide, the oligonucleotide may be amplified using labeled primers, and the labeled extended primers determined.

For convenience, kits may be provided having particles with primers for particular snp determinations, usually having at least about 50 particles, more usually at least about 500 particles, and may have 1,000 or more different particles. In addition, the kit may include a template dependent nucleotide extending enzyme, magnetic particles comprising members of a specific binding pair, labeled terminating nucleotides, where the label is a member of a specific binding pair.

The subject methodology provides a simple, rapid and accurate method for identifying a large number of snps associated with an individual genome or other DNA source. The snps can be determined in a single or few assay mixtures. Using primers as probes which are directed to specific target DNA known to have snps of interest, the protocol may be used for diagnosis, identification, forensics, genetic disease relationships, research or the like. With a relatively limited number of coding compounds, by using combinations of coding compounds, more than 10,000 different snps may be identified. Capillary electrophoresis allows for a single eletropherogram, which may be directly read and with signal processing, the number and nature of snps can be provided in chart or table. In this way, genomes of related family groups may be compared, diseases or other physiological condition associated with specific snps or patterns of snps. As more is learned about the role of snps in the development and health of individuals, including species other than humans, such as domestic animals, plants, fish, etc., the ability to rapidly identify snps from the genome will be a very powerful tool to relate individuals of a species, relate phenotypes to specific snps, etc., Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining a plurality of single nucleotide polymorphisms in a sample of target DNA, the method comprising the steps of:

providing a plurality of primers and coding members attached to particles such that each particle has a unique primer and a unique coding member indicative of the primer, the primer of each particle being complementary to a site on a target DNA in the sample, each site being adjacent to a nucleotide having a single nucleotide polymorphism, the coding member of each particle being attached by a releasable linkage to the particle and having a molecular weight of between 100 daltons and 20 kilodaltons, and the releasable linkage being thermally, photolytically, or chemically labile;

combining the particles with the sample such that each of the primers anneals to the target DNA and is enzymatically extended to form an extended primer by adding to such primer a label indicative of the nucleotide having a single nucleotide polymorphism;

separating particles having extended primers by the labels added to such primers;

releasing the coding members from the particles having extended primers after such separation by thermally, photolytically, or chemically cleaving the releasable linkages thereof; and electrokinetically separating the coding members to form an electropherogram having a specific band for each coding member so that the plurality of single nucleotide polymorphisms is determined.

2. The method of claim 1 wherein said step of combining includes extending said primer by a polymerase to add a terminating nucleotide having said label.

3. The method of claim 2 wherein said label is a fluorophore.

4. The method of claim 3 wherein said step of separating said particles includes sorting said particles according to said fluorophore of said terminating nucleotide.

5. The method of claim 2 wherein said label is a binding member of a specific binding pair.

6. The method of claim 5 wherein said binding member is selected from the group consisting of biotin, digoxin, fluorescein, and 2,4-dinitrobenzene.

7. The method according to claim 1, 2, 3, 4, 5, or 6 wherein said plurality of said primers and said coding members is between 10 and 50.

8. The method of claim 7 wherein said step of electrokinetically separating said coding members includes separating said coding members by capillary electrophoresis.

* * * * *